Figure 1:
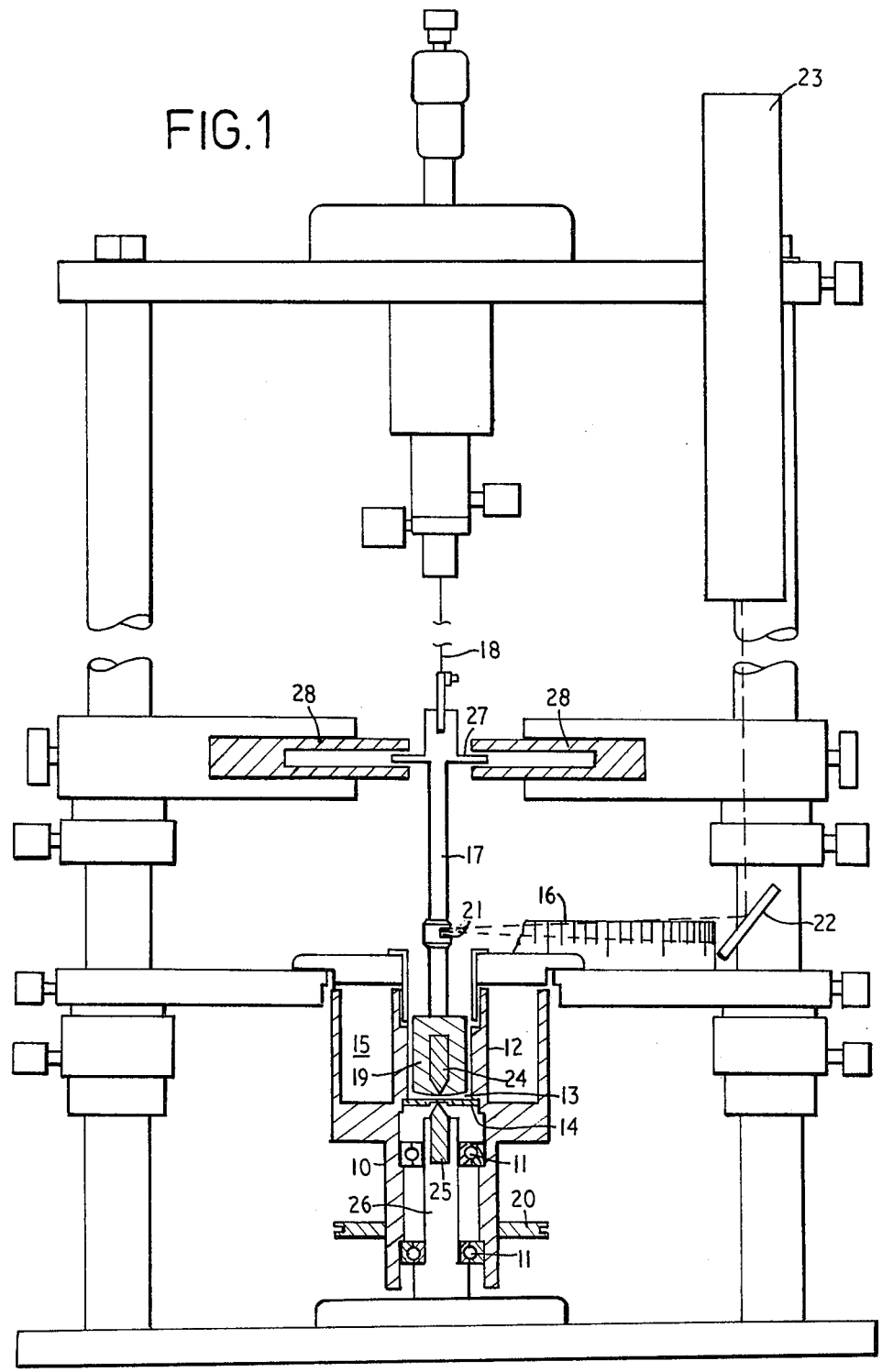

United States Patent [19]

Palmer

[11] 4,045,999
[45] Sept. 6, 1977

[54] ROTATIONAL VISCOMETERS

[75] Inventor: Alexander Allan Palmer, St. Ives, Australia

[73] Assignee: Sydney Hospital, Sydney, Australia

[21] Appl. No.: 739,267

[22] Filed: Nov. 5, 1976

[51] Int. Cl.² .................................. G01N 11/14
[52] U.S. Cl. ............................................ 73/59
[58] Field of Search ................................ 73/59, 60

[56] References Cited

U.S. PATENT DOCUMENTS 3,122,914  3/1964  Stabe et al. .............................. 73/59

FOREIGN PATENT DOCUMENTS 26,840     9/1970  Japan ....................................... 73/59
12,518     6/1968  Japan ....................................... 73/59
1,120,925  7/1968  United Kingdom ..................... 73/59

Primary Examiner—Jerry W. Myracle
Assistant Examiner—Joseph W. Roskos
Attorney, Agent, or Firm—Henry R. Lerner

[57] ABSTRACT

In a rotational viscometer the provision of magnetic means which maintains the rotating member coaxial with the torsional cylinder which is rotationally deflected in proportion to the viscosity of fluid under test.

3 Claims, 4 Drawing Figures

ROTATIONAL VISCOMETERS

The present invention relates to rotational viscometers and more particularly to a frictionless centring mechanism for use in a rotational viscometer. Rotational viscometers consist essentially of two members, separated by the fluid under test which rotate relative to one another about a common vertical axis. The rotation of one member tends to drag the other member round with it and the relationship between the angular velocity of the rotating member and the torque developed on the other member characterizes the viscous properties of the fluid. One of the uses to which rotational viscometers are put is to measure the viscosity of blood, the viscosity of which varies with the rate of shearing and it is possible with such an instrument to measure the viscosity at a range of different shear rates.

The geometry of the two members may take several forms of which coaxial cylinders, coaxial cones and cone and plate forms are examples. The present invention can be applied to many forms of rotational viscometer but is particularly applicable to one simple and convenient form of coaxial rotating cylinder viscometer which consists of an outer cylindrical member mounted for rotation about a vertical axis, the cylindrical member defining a cavity for the reception of a quantity of blood or other liquid, the cavity being cylindrical and coaxial with the body, there being within the cavity a torsion cylinder which is suspended by means of a vertically extending torsion strip, the torsion cylinder being maintained in a coaxial relationship with the cylindrical member. In use the space between the torsion cylinder and the cavity walls of the cylindrical member is filled with liquid, and on rotation of the cylindrical member the torque is applied to the torsion cylinder by reason of the viscosity of the liquid which causes it to twist against the restoring force of the torsion strip. The degree of twisting is a measure of the viscosity of the liquid. Suitable driving means are provided for rotating the cylindrical member at a range of different speeds, for example, for 0.1 rpm to 400 rpm. This is usually done by means of a synchronous motor driving through a variable ratio gearbox and a belt drive.

In order to obtain accurate results, it is necessary to maintain the torsion cylinder as nearly as possible coaxial with the cavity in the cylindrical member, without the introduction of friction which would affect the accuracy of the results. At low speeds of rotation gravity may suffice to maintain the torsion cylinder coaxial but at higher speeds of rotation of the rotating member, the torsion cylinder develops an orbital rotary movement which interferes with the measurements.

The invention consists in the provision in a rotational viscometer of magnet means acting to maintain the rotating member coaxial with the other member during rotation.

Figures 2A, 2B, 2C:
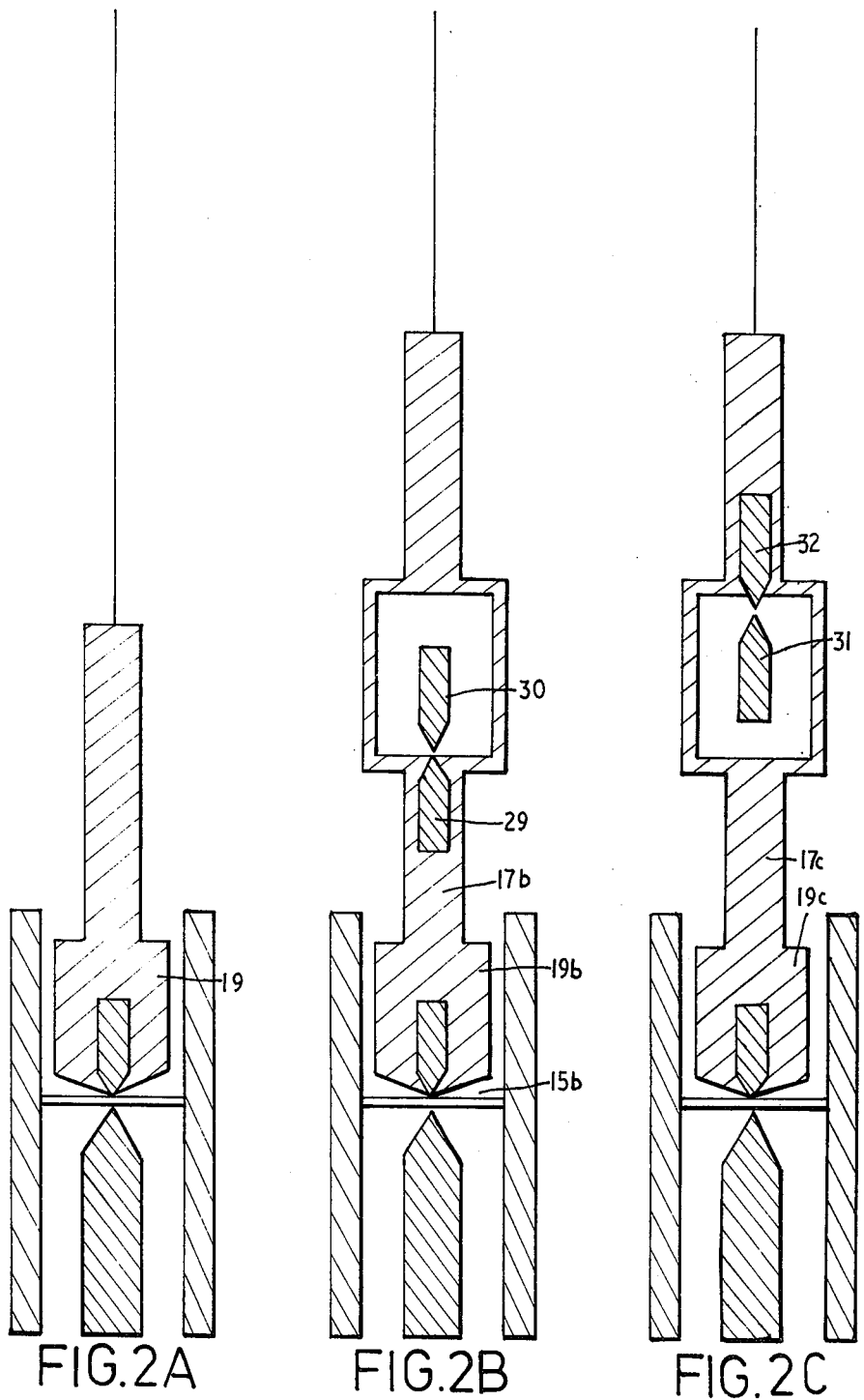

In order that the nature of the invention may be better understood, preferred forms thereof are hereinafter described by way of example, with reference to the accompanying drawings in which:

FIG. 1 is a cross-sectional elevation of a rotational viscometer incorporating the invention and FIGS. 2a, 2b, and 2c illustrate three alternative arrangements of centring magnets.

The apparatus shown in FIG. 1 consists of an outer rotatable cylindrical member 10 supported on ball bearings 11. An inner wall 12 of the member 10 defines a cylindrical cavity 13 which acts as a receptacle for the liquid, for example blood, the viscosity of which is to be measured. The bottom 14 of the cavity 13 is constituted by an electrically non-conducting material to avoid the formation of eddy currents. An annular cavity 15 which may be filled with a liquid maintained at a substantially constant temperature surrounds cavity 13 to maintain the contents of the cavity 13 at a constant temperature.

It should be emphasised that the drawing is purely diagrammatic and details of construction that are conventional in rotational viscometers but not specifically related to the invention have been omitted or not described.

A spindle 17 is supported by a torsion strip 18 which may be, for example, of copper-beryllium alloy and has at its lower end a torsion cylinder 19 which lies coaxially within the cylindrical cavity 13. The cylindrical member 10 is rotated by means of a belt not shown driving the pulley 20 at the lower end of the member 10. Rotation of the member 10 acts through the viscosity of the liquid contained in the cavity 13 to cause rotation of the torsion cylinder 19 against the restoring force of the torsion strip 18, and if the member 10 is rotated at a constant rate, the torsion cylinder 19 will take up fixed position involving a degree of angular deflection which may be read on a suitable scale 16 and which is a measure of the viscosity of the liquid at the particular rate of rotation given to the member 10. In the apparatus illustrated a mirror 21 is provided on the spindle 17 which reflects a light beam, reflected on to it by the mirror 22 from a light source 23, on to the scale 16.

As stated above it is necessary to maintain the torsion cylinder 19 coaxial with the cavity 13 and it is with this aspect of the apparatus that the present invention is concerned. In order to achieve this result a magnet 24 is contained within the torsion cylinder 19 and a corresponding magnet 25 is supported immediately below it in the stationary spindle 26 which supports the ball bearings 11. Both magnets are permanent magnets of a material such as that known as "Alnico" and both are tapered to a point at their adjacent ends. The apparatus is set up so that the torsion cylinder 19 is in a coaxial relationship with the cavity 13 and it is found that by reason of the magnetic field exerted by the magnets 21 and 22 this relationship is maintained very closely during rotation of the torsion cylinder, without the introduction of additional friction to the system. The magnet 25 exerts a downward force on the torsion strip 18 which has been found beneficial in the operation of the apparatus.

In this particular embodiment of the invention the spindle 17 is provided with a disc 27 which rotates within a damping magnet 28 which acts not only to damp the movement of the torsion cylinder 19 but also assists in centering the spindle 17. It has been found however that in many applications, damping is not necessary.

The arrangement of centring magnets used in FIG 1 is shown diagrammatically in FIG. 2a. In an alternative arrangement illustrated in FIG. 2b a further pair of centring magnets 29 and 30 is provided at the upper end of the torsion cylinder 19b. These magnets are arranged and shaped in a somewhat similar manner to magnets 24 and 25, one magnet 29 being affixed in the spindle 17b on the axis of the torsion cylinder 19b and the other magnet 30 being supported in stationary condition by suitable support means not shown. The use of these additional magnets provides more accurate centring of the torsion cylinder which may be found necessary in some applications, but it also complicates the structure of the apparatus considerably in that in order to remove the torsion cylinder 19b from the cavity 15b, for cleaning purposes, the upper fixed magnet 30 must be removed.

FIG. 2c shows a further alternative arrangement in which a fixed magnet 31 is arranged below a magnet 32 mounted in the spindle 17c coaxially with the torsion cylinder 19c.

The embodiments of the invention described above are given by way of example only as preferred forms of the invention within the general scope thereof as defined above.

I claim:

1. A rotational viscometer consisting of a first member and a second member, relatively rotatable about a common vertical axis, the member between them defining a cavity for the reception of a fluid under test, means for rotating the first member, a permanent magnet arranged within the second member and on the said axis, a second permanent magnet arranged on the said axis adjacent the first magnet, the arrangement being such that the magnets interact to maintain the members coaxial during rotation of the first member, said first member being a hollow vertically extending cylinder open at its upper end defining within it a cavity for the reception of a fluid to be tested, said cavity having a floor of electrically non-conductive material, and said second member being a cylinder arranged within the said cavity, the permanent magnet arranged within said second member tapering to a point on the said axis at its lower end, the second magnet being supported immediately below the floor of the said cavity, the upper end thereof being tapered to a point lying on said axis.

2. A rotational viscometer as claimed in claim 1, wherein an additional pair of magnets is arranged on said axis to reinforce the action of said magnets, one of said additional pair of magnets being associated with said second member and the other being stationary.

3. A rotational viscometer consisting of a first member and a second member, relatively rotatable about a common vertical axis, the member between them defining a cavity for the reception of a fluid under test, means for rotating the first member, a permanent magnet arranged within the second member and on the said axis, a second permanent magnet arranged on the said axis adjacent the first magnet, the arrangement being such that the magnets interact to maintain the members coaxial during rotation of the first member, and an additional pair of magnets arranged on said axis to reinforce the action of said magnets, one of said additional pair of magnets being associated with said second member and the other being stationary.

* * * * *